US00PP18932P3

(12) United States Plant Patent
Philpott

(10) Patent No.: US PP18,932 P3
(45) Date of Patent: Jun. 17, 2008

(54) ***VERONICA* PLANT NAMED 'GLORY'**

(50) Latin Name: *Veronica spicata*
Varietal Denomination: Glory

(76) Inventor: Heather Philpott, Bethany, Luston, Nr. Leominster, Herefordshire HR6 0EB (GB)

( * ) Notice: Subject to any disclaimer, the term of this patent is extended or adjusted under 35 U.S.C. 154(b) by 664 days.

(21) Appl. No.: 09/728,748

(22) Filed: Dec. 2, 2000

(65) Prior Publication Data

US 2002/0069442 P1 Jun. 6, 2002

(51) Int. Cl.
*A01H 5/00* (2006.01)

(52) U.S. Cl. ..... Plt./251
(58) Field of Classification Search ..... Plt./251
See application file for complete search history.

(56) References Cited

PUBLICATIONS

UPOV–ROM GTITM Computer Database 2005/05, GTI Jouve Retrieval Software, citation(s) for 'Glory' Oct. 10, 2000.*

The new Royal Horticultural Society. Dictionary of gardening 1992. V. 4 p. 652.

* cited by examiner

*Primary Examiner*—Kent Bell
*Assistant Examiner*—Annette H Para

(57) ABSTRACT

A new cultivar of *Veronica* plant named 'Glory' that was discovered in a cultivated area and is characterized by a dense compact habit and abundant, long-blooming, compact flower spikes of a deep violet color. These combined traits set it apart from all other existing varieties of *Veronica* known to the inventor.

3 Drawing Sheets

BACKGROUND OF THE INVENTION

The present invention relates to a new and distinct cultivar of Speedwell known botanically as *Veronica spicata* and referred to hereinafter by the cultivar name 'Glory'. The new invention was discovered in a cultivated area as a chance seedling from the inventors garden in Detling, Kent, England. 'Glory' was discovered in the summer of 1987, growing amongst numerous cultivars of *Veronica spicata.* The exact parents are unknown.

'Glory' is distinguished from all other *Veronicas* by its dense compact habit, production of an abundance of compact flower spikes and the deep violet color of the flowers. The closest comparison varieties are *Veronica,* 'Sunny Border Blue' (not patented), *Veronica,* 'Goodness Grows' (not patented) and 'Foersters Blue' (not patented). The new invention is uniquely different from 'Sunny Border Blue' (not patented) in its dense compact habit and its smooth vigorous green leaves that are retained throughout the season. The leaves of 'Sunny Border Blue' (not patented) are larger and crinkled with a dehydrated appearance, and the lower leaves tend to drop off due to disease. In contrast to 'Goodness Grows' (not patented), *Veronica* 'Glory' exhibits a dense habit and the flowers exhibit more violet color than blue. In contrast to 'Foersters Blue' (not patented), 'Glory' exhibits a compact habit, dark green leaves, dark violet-blue, and compact flower spikes that continue flowering for a two month period or longer when spent flowers are removed. 'Foersters Blue' (not patented) is tall and leggy with pale blue flowers and pale green leaves.

'Glory' was observed by the inventor over a period of approximately seven years, during which time the plant was found to retain its unique characteristics. In 1995, the first asexual propagation was conducted by the inventor, using the method of division. The new invention was first asexually propagated in Herefordshire England. Since that time under careful observation, successive generations have been determined stable and uniform.

SUMMARY OF THE INVENTION

The new invention *Veronica* 'Glory' can be distinguished from all other known varieties of *Veronica* by the following characteristics:

1. A dense, compact habit.
2. Violet colored flowers.
3. An abundance of flowers that bloom profusely.
4. A long blooming period when spent flowers are removed.
5. Compact flower spikes. In combination these characteristics set 'Glory' apart from all other existing varieties.

BRIEF DESCRIPTION OF THE DRAWINGS

The accompanying color photographs illustrate the distinguishing traits of the new cultivar 'Glory'.

Sheet 1 shows a side view of the entire plant in a two-gallon container, illustrating the foliage, profuse flowering and plant habit.

Sheet 2 shows a close-up of the leaf flower and buds.

Sheet 3 illustrates a close-up of a flower spike. All photographs are taken using conventional techniques and although foliage colors may appear different from actual colors due to light reflectance, they are as accurate as possible by conventional photography.

BOTANICAL DESCRIPTION OF THE PLANT

The following is detailed description of the *Veronica* cultivar named 'Glory'. Data was collected in Arroyo Grande, Calif. from 12 month old plants grown in two-gallon containers. Phenotypic differences may be observed with variations in environmental, climatic, and cultural conditions, without however, any difference in genotype. Color determinations are in accordance with The Royal Horticultural Society Color Chart except where general color terms of ordinary dictionary significance are used. The growing requirements are similar to the species.

Botanical classification: *Veronica spicata* 'Glory'.
Common name: Speedwell.
Type: Herbaceous perennial.
Use: Border plant.
Parentage: Exact parents unknown. 'Glory' is a chance seedling that arose in a garden collection of numerous cultivars of *Veronica spicata*.
Growth rate: Vigorous.
Branching habit: Erect or ascending.
Mature height: 40–45 cm in height.
Mature width: Approximately 30 cm in width.
Hardiness: Zone 3.
Propagation method: Cuttings and division.
Growth habit: Dense and compact.
Root system: Fibrous.
Soil: Plant in well-drained soil.
Light levels: Plant in full sun.
Special needs: A longer flowering period can be encouraged by removing spent flowers.
Time to initiate roots: 2 weeks to develop from an initial cutting to a rooted cutting.
Time to develop to a one-gallon: 4 months to develop from a rooted cutting to a one gallon.
Diseases and pests: Susceptible to mildew under dry conditions and not known resistance to pests.
Seasonal interest. A profusion of violet flowers in summer.
Stem:
*Shape.*—Cylindrical.
*Surface.*—Sparsely puberulent with long and short hairs.
*Length.*—10 cm in length.
*Width.*—25 cm in width.
*Secondary stems.*—10 cm in length by 0.25 cm in width.
*Color.*—138B.
*Internodes.*—2–3 cm long between nodes.
Foliage:
*Leaf arrangement.*—Opposite.
*Leaf division.*—Simple.
*Leaf shape.*—Narrow ovate.
*Leaf tip.*—Acute, somewhat acuminate.
*Leaf base.*—Rounded.
*Petiole size.*—1 cm in length by 1 mm in width.
*Leaf margins.*—Serrate.
*Leaf surface.*—Glabrous on upper and lower surfaces.
*Venation.*—Pronounced mid-vein protruding on lower surface and depressed on upper leaf surface.
*Vein color.*—147B on under surface and 146A on upper surface.
*Secondary veins.*—Approximately six very small veins branching off on both sides of mid-vein.
*Length of leaf.*—6–7 cm in length.
*Width of leaf.*—2 cm in width.
*Color of mature leaf* (*lower surface*).—137C.
*Color of mature leaf* (*upper surface*).—137A.
*Color of young leaf* (*upper surface*).—137B.
*Color of young leaf* (*lower surface*).—137D.
*Foliar fragrance.*—None observed.
*Diseases.*—Potential for mildew.
Flower:
*Type.*—Glomerate; densely cluster flowers.
*Number of petals.*—Four petals.
*Color of petals.*—88A to 89A.
*Size of petals.*—4 mm in length by 2–3 mm in width.
*Fragrance.*—None observed.
*Arrangement of inflorescence.*—Terminal thyrse.
*Shape of petal.*—Elliptic.
*Margins of petal.*—Entire.
*Surface of petal.*—Glabrous.
*Inflorescence.*—Raceme.
*Size of inflorescence.*—Ranges from 2 cm to 15 cm in height and about 1.5 cm in width.
*Quantity of inflorescence.*—Five to fourteen per stalk.
*Flower longevity.*—Flowers last 3 to 3,5 weeks.
*Peduncle size.*—3–5 cm in length and 1 mm in width.
*Peduncle surface.*—Pubescent with long hairs.
*Peduncle color.*—138B.
*Blooming time.*—Diurnal.
*Months of flowering.*—June and July.
*Calyx.*—Three sepals.
*Calyx color.*—137A.
*Size of sepals.*—1 mm in width by 3 mm in length, with linear subtending bracts 6 mm in length and 1 mm in width.
*Color of bracts.*—141C.
*Surface of bracts.*—Pubescent.
*Bud size.*—1.5 mm in width by 1 mm in length.
*Bud color.*—89A.
Reproductive organs:
*Pistil.*—One, violet-blue 93A.
*Size of pistil.*—3 mm in length by 1 mm in width.
*Base of throat.*—Flocculent white hairs 155 C at base of pistil.
*Stamens.*—Two.
*Stamen color.*—155C.
Seed production: Seed production has not been observed.

It is claimed:

1. A new and distinct variety of *Veronica* plant named 'Glory' as described and illustrated.

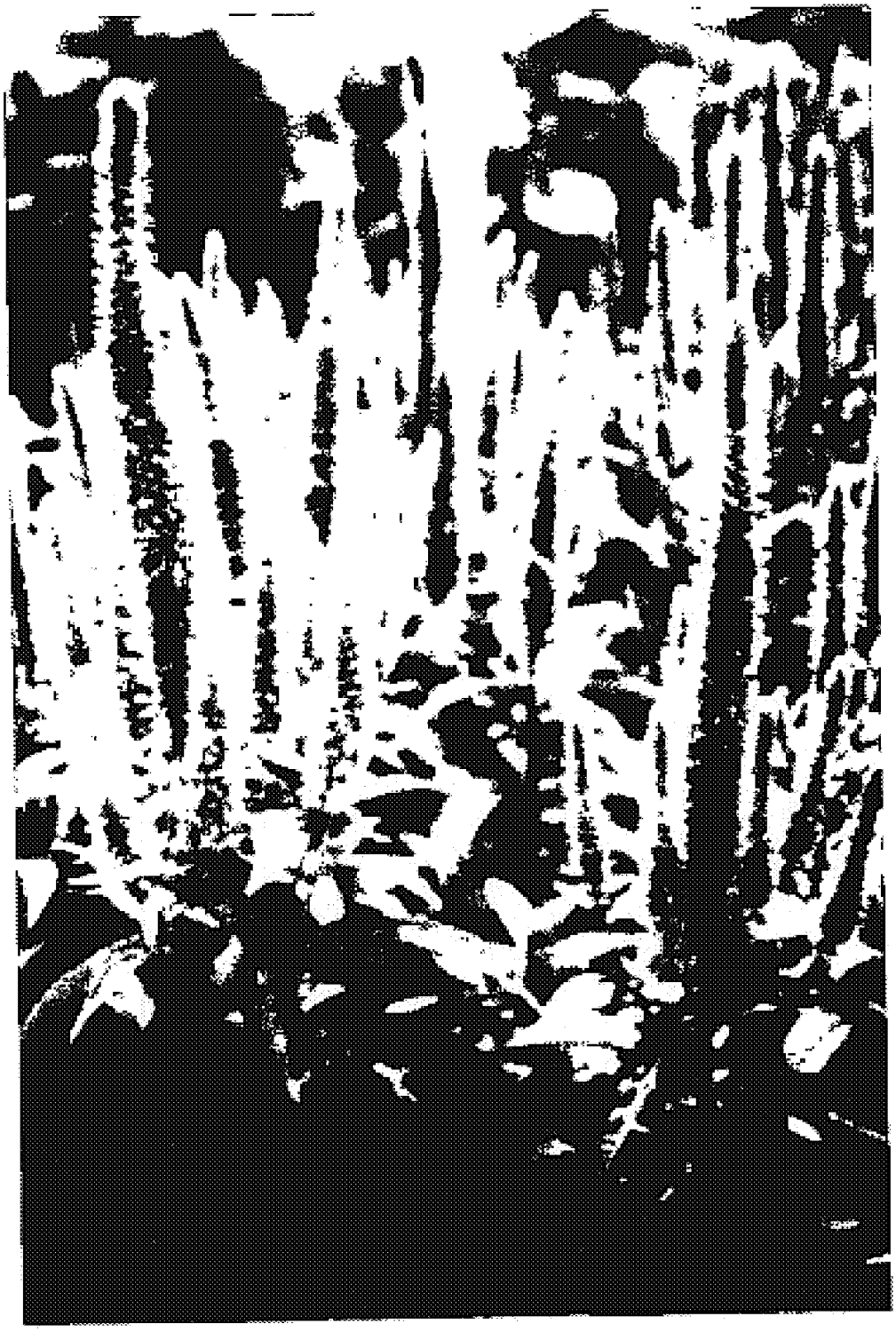

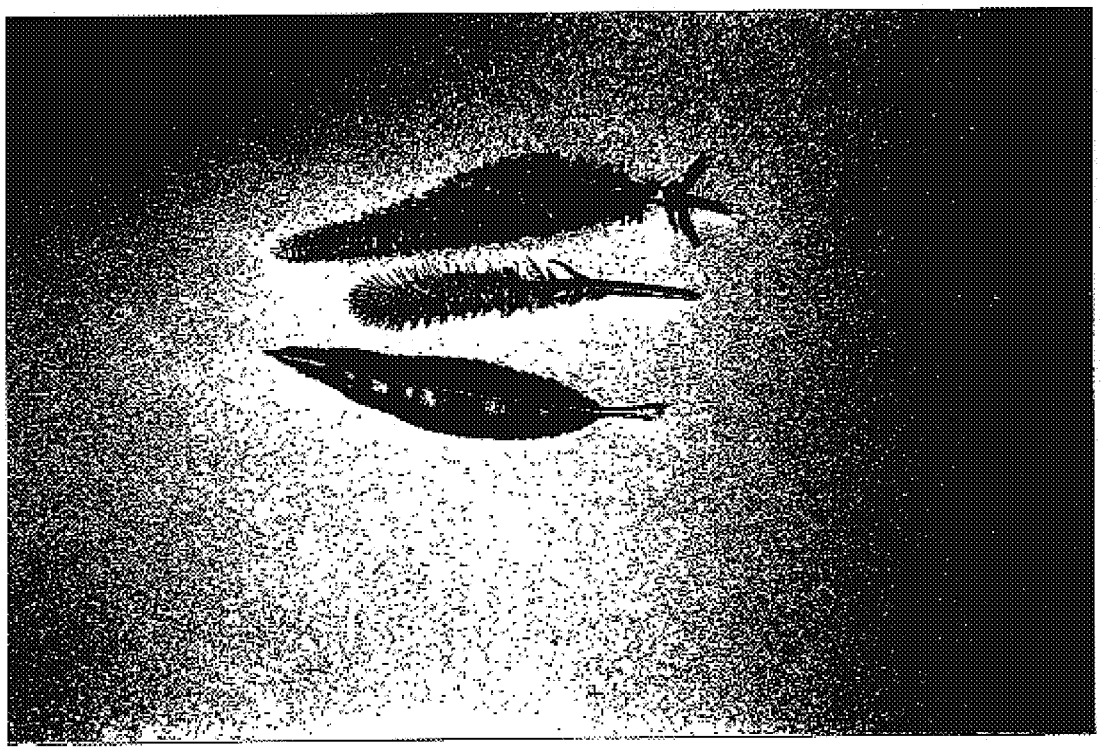

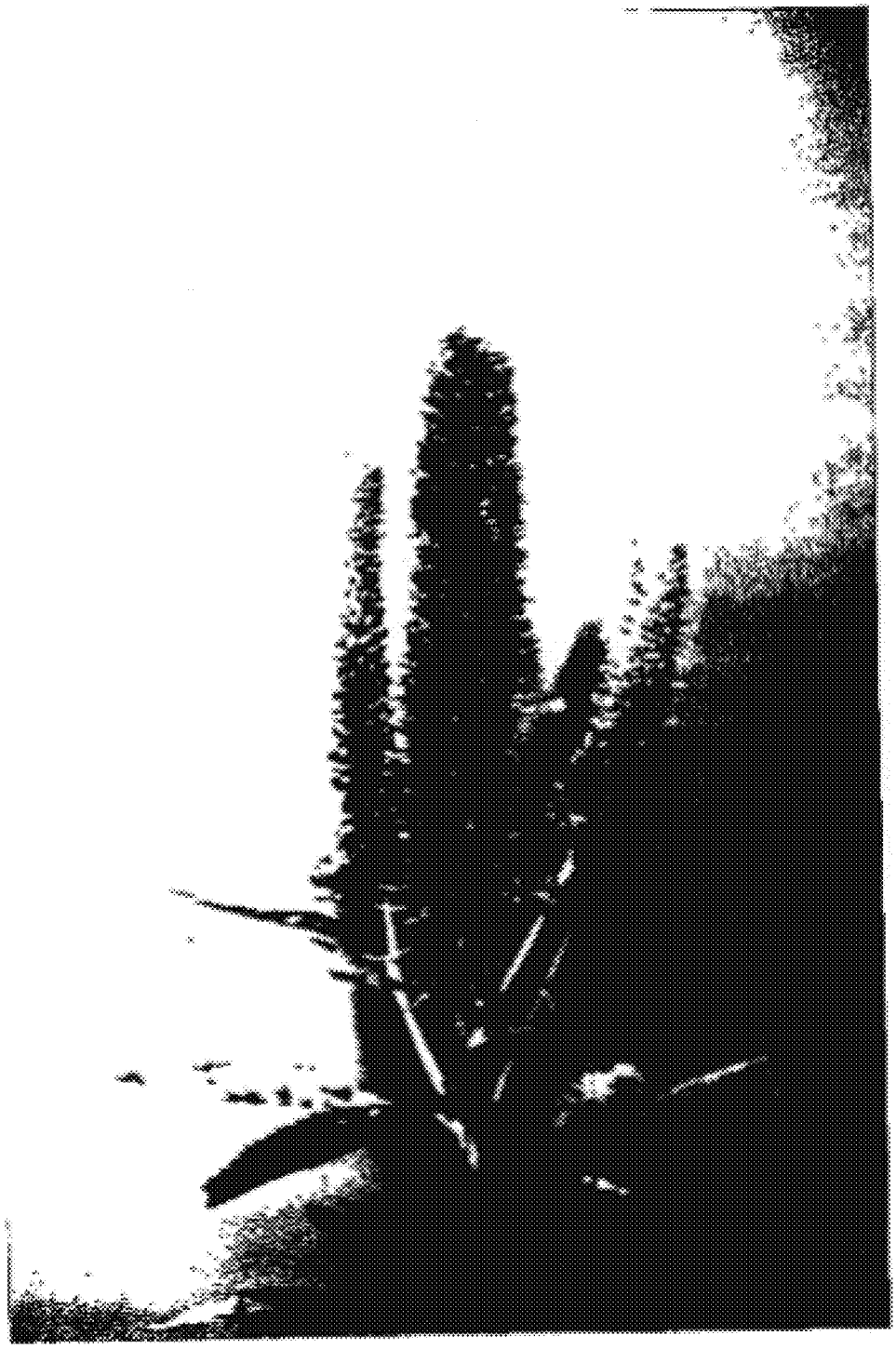

* * * * *